(12) United States Patent
Djupevåg et al.

(10) Patent No.: US 11,286,448 B2
(45) Date of Patent: Mar. 29, 2022

(54) ENZYMATIC PROCESSING PLANT AND METHOD OF ENZYMATIC PROCESSING

(71) Applicant: ALKYMAR AS, Haugsvær (NO)

(72) Inventors: Olav Asle Djupevåg, Bønes (NO); Torstein Frantzen, Bergen (NO)

(73) Assignee: ALKYMAR AS, Haugvaer (NO)

( * ) Notice: Subject to any disclaimer, the term of this patent is extended or adjusted under 35 U.S.C. 154(b) by 281 days.

(21) Appl. No.: 15/510,278

(22) PCT Filed: Sep. 14, 2015

(86) PCT No.: PCT/EP2015/070942
§ 371 (c)(1),
(2) Date: Mar. 10, 2017

(87) PCT Pub. No.: WO2016/041896
PCT Pub. Date: Mar. 24, 2016

(65) Prior Publication Data
US 2017/0247649 A1    Aug. 31, 2017

(30) Foreign Application Priority Data

Sep. 15, 2014   (GB) .................................... 1416283

(51) Int. Cl.
| | |
|---|---|
| *C12M 1/40* | (2006.01) |
| *B01F 5/06* | (2006.01) |
| *C12M 1/02* | (2006.01) |
| *B63B 35/14* | (2006.01) |
| *C12M 3/06* | (2006.01) |
| *C12M 1/00* | (2006.01) |
| *C12P 21/06* | (2006.01) |

(52) U.S. Cl.
CPC ............. *C12M 21/18* (2013.01); *B01F 5/065* (2013.01); *B01F 5/0647* (2013.01); *B01F 5/0655* (2013.01); *B63B 35/14* (2013.01); *C12M 27/00* (2013.01); *C12M 27/16* (2013.01); *C12M 29/04* (2013.01); *C12M 41/22* (2013.01); *C12P 21/06* (2013.01); *B01F 2215/0073* (2013.01); *B01F 2215/0431* (2013.01); *B01F 2215/0477* (2013.01); *B01F 2215/0481* (2013.01)

(58) Field of Classification Search
CPC ...... C12M 21/18; C12M 27/00; C12M 31/22; C12M 1/40; C12P 21/06; B63B 35/14; B01F 5/065; B01F 5/0655; B01F 5/0647; B01F 2215/0431; G01F 2215/0073
See application file for complete search history.

(56) References Cited

U.S. PATENT DOCUMENTS

| | | | | |
|---|---|---|---|---|
| 4,126,517 A | * | 11/1978 | Bayer | ..................... B01F 5/102 |
| | | | | 435/262 |
| 4,434,229 A | * | 2/1984 | Nankai | .................. C12N 11/02 |
| | | | | 435/174 |
| 6,258,575 B1 | * | 7/2001 | Shimizu | ................. C12N 11/02 |
| | | | | 435/134 |

FOREIGN PATENT DOCUMENTS

WO    WO-2004049818 A1 *  6/2004  .............. A23J 1/002

* cited by examiner

*Primary Examiner* — Susan M Hanley
*Assistant Examiner* — Paul C Martin
(74) *Attorney, Agent, or Firm* — Eversheds Sutherland (US) LLP (57) ABSTRACT

An enzymatic processing plant for continuous flow-based enzymatic processing of organic molecules. The enzymatic processing plant including an enzymatic processing area, wherein the enzymatic processing area includes a turbulence-generating pipe with a repeatedly changing centre-line and/or a repeatedly changing cross-section, for generating turbulence to mix a reaction mixture and prevent sedimentation of particles as the reaction mixture is flowing through the turbulence-generating pipe. The enzymatic processing plant and the enzymatic processing area are arranged such that the reaction mixture is subjected to turbulence within the enzymatic processing area for a reaction time of 15 minutes or more.

12 Claims, 3 Drawing Sheets

ENZYMATIC PROCESSING PLANT AND METHOD OF ENZYMATIC PROCESSING

TECHNICAL FIELD

The present invention relates to an apparatus and method for enzymatic processing of organic molecules, for example, enzymatic hydrolysis of organic molecules. Organic molecules include macromolecules, for example proteins, lipids and polysaccharides.

BACKGROUND OF THE INVENTION

Enzymatic processing of organic molecules encompasses at least the following processes: oxidation/reduction (by oxidoreductases), transfer of a functional group, e.g. a methyl or phosphate group (by transferases), hydrolysis (by hydrolases), cleavage of various bonds by means other than hydrolysis and oxidation (by lyases), isomerization changes within a single molecule (by isomerases) and joining of two molecules with covalent bonds (by ligases).

In enzymatic hydrolysis, chemical bonds in a molecule are broken by the addition of water, with an enzyme acting as a catalyst for the reaction. To promote this reaction, the various components of the reaction mixture (for example, the raw material comprising the molecules to be hydrolysed, water, and an appropriate enzyme) must be mixed together under appropriate reaction conditions. As an example, proteins obtained from marine biological sources (e.g. algae, or fish-derived material) can be processed by hydrolysis to obtain a wide array of peptides all the way down to single amino acids—depending on the enzymes used and the processing conditions.

Mixing the various components of the reaction mixture is necessary, regardless of whether the reaction taking place is hydrolysis or is another form of enzymatic processing. Thus, whilst hydrolysis is the focus of the following discussion, the technical considerations and the invention itself are equally applicable to enzymatic processing more generally.

WO-A-2004/049818 discloses a plant for hydrolysis of protein-containing raw material. The plant includes a hydrolysis area comprising a pipe in which is provided a rotating auger to convey and gently mix the reaction mixture. It is recognised that mixing must be carried out in a controlled manner to control contact between the enzymes and raw material, whilst avoiding (or minimizing the degree of) formation of an emulsion. The process can be run as a continuous process or as a batch process.

Active mixing in this way can lead to the disadvantage that the mixing forces are not evenly distributed throughout the bulk of the flow. This can lead to concentration of mechanical stress within the system, and formation of zones in which the reaction mixture is poorly mixed. The system has a further disadvantage in that the complexity, weight and cost of the system are increased by provision of the auger. Additionally, residue and deposits can build up on the auger, so the auger will need to be periodically cleaned. However, due to its complex shape, the auger is not easy to clean. The time and effort necessary to clean the auger increases the cost of running the system, and decreases its efficiency due to the necessary downtime whilst the auger is cleaned.

EP-B-0566877 discloses an apparatus for the enzymatic hydrolysis of proteins, in which hydrolysis is carried out in a tube provided with static mixing elements. The static mixing elements comprise metal or plastic braces nested into each other. However, this apparatus may not be able to perform the same hydrolysis reactions as are described in WO-A-2004/049818, since it is not possible to have a continuous reaction process with the apparatus of EP-B-0566877.

Moreover, the static mixing elements are difficult to clean (leading to increased downtime and reduced efficiency) and also increase the complexity, weight and cost of the system. Additionally, the mixing forces generated by the static mixing elements may not be evenly distributed throughout the bulk of the reaction mixture flow, potentially leading to formation of zones in which the reaction mixture is poorly mixed.

SUMMARY OF THE INVENTION

Therefore, in view of problems with the prior art, there is a need to provide an alternative means of mixing the various reagents in the hydrolysis area, or more generally in an enzymatic processing area of an enzymatic processing plant.

According to a first aspect of the present invention, there is provided a continuous flow-based enzymatic processing plant for enzymatic processing of organic molecules comprising: an enzymatic processing area, wherein the enzymatic processing area comprises a turbulence-generating pipe with a repeatedly changing centre-line and/or a repeatedly changing cross-section, for generating turbulence to mix a reaction mixture and prevent sedimentation of particles as the mixture is flowing through the turbulence-generating pipe, and wherein the enzymatic processing plant and the enzymatic processing area are arranged such that the reaction mixture is subjected to turbulence within the enzymatic processing area for a reaction time of 15 minutes or more.

According to a second aspect of the present invention, there is provided a method of continuous flow based enzymatic processing of organic molecules comprising: passing a reaction mixture through an enzymatic processing area including a turbulence-generating pipe, the turbulence-generating pipe having a repeatedly changing centre-line and/or a repeatedly changing cross-section, the turbulence generated by the turbulence-generating pipe being used to mix the reaction mixture and to prevent sedimentation of particles as the mixture is flowing through the turbulence generating pipe, wherein the reaction mixture is subjected to turbulence within the enzymatic processing area for a reaction time of 15 minutes or more.

By the use of a turbulence generating pipe having a repeatedly changing centre-line and/or a repeatedly changing cross-section then turbulence is generated without the need for mixing mechanisms with moving parts or for static mixing elements of the type shown in EP-B-0566877. Mixing by turbulence in the pipe has an important advantage compared to stirring or static mixers as in the prior art; the mixing forces are distributed throughout the entire bulk. This reduces both stress concentration and formation of zones with poor mixing.

Moreover, prior art using mixing elements in flow pipes such as those in EP-B-0566877, or even prior art using corrugated pipework as in U.S. Pat. No. 4,126,517, does not allow for the continuous flow of heterogeneous biological substrates while maintaining thorough mixing for extended periods of time without clogging or sedimentation of solid particles. It is important to allow for long reaction times of at least 15 minutes and preferably longer, for example 20 minutes or more, 30 minutes or more, or even longer reaction times as set out below. The reaction times can be achieved by a combination of slow flow rates and pipework of sufficient length, again as discussed below. In the prior art referenced above the flow rates are too fast and the pipework is too short for the required reaction times in a continuous flow process.

As a result of turbulent flow through the turbulence-generating pipe, the reaction mixture is mixed and maintained as a homogenous mixture through the process. The turbulence also reduces the risk of sedimentation. Depending on the actual particle composition of the feedstock and the flow velocity then the turbulence can entirely prevent the heavier phases of the reaction mixture from settling.

Whilst a degree of turbulence is important for mixing the reaction mixture, it is also desirable to reduce (and ideally to minimise) the generation of shear forces in the pipe. Shear forces are caused by a fluid velocity that is too high, and can contribute towards the production of emulsions, which is undesirable.

Avoiding or reducing the formation of emulsions is an important consideration in enzymatic processing systems (for example, hydrolysis of protein/lipid mixtures). Emulsions block enzymatic access to parts of the feedstock trapped in emulsions and thus reduce the efficiency of enzymatic processing. Furthermore, the problem with emulsions extends to the separation stage. In emulsions, lipids may be tightly associated with water-soluble components such as peptide material which mechanical separators are unable to separate. Thus the result can be poor separation with, for example, lipid in the protein phase and/or protein in the lipid phase. Emulsions can be taken out by filtration at a later stage, but the emulsified components still cannot be recovered and combined with the non-emulsified fractions. That is, without specific equipment it is not possible to separate water-soluble components from the emulsion to recombine them with the non-emulsified water-soluble fraction, and nor is it possible to separate lipids and lipid-soluble components from the emulsion to recombine them with the non-emulsified lipid and lipid-soluble fraction.

It will be appreciated from the foregoing that the challenge is to obtain good mixing of the reaction mixture, without producing emulsions. Additionally, a minimum flow velocity is required to prevent solid particles from clogging the pipe. The proposed turbulence generating pipe using repeatedly varying cross-section and/or centre-line is able to generate turbulence at lower flow velocities and with reduced shear stresses compared to prior art static mixers and the like. By combining this type of a pipe with long reaction times and a continuous flow process it is possible to effectively perform enzymatic processing that is either not possible with the prior art, or that requires complex and hard to clean equipment, often restricted to batch processing.

The enzymatic processing may be enzymatic hydrolysis. The reference to a continuous flow process is intended to cover a process where the flow through the processing plant occurs in a single pass, without repeated circuits or batch-wise processing, with the reaction mixture entering the processing plant continuously and the product of the reaction exiting the processing plant continuously. Depending on the nature of the reaction there may be further raw materials added continuously partway through the process and/or products may be removed continuously partway through the process, for example oil soluble components may be continuously removed via a separator and so on.

The turbulence-generating pipe may be a tube, a hose, or the like. It may be rigid or flexible. The enzymatic processing area may be made up of a single pipe such that the reaction time occurs entirely within one turbulence generating pipe. Alternatively the enzymatic processing area may be made up of multiple turbulence generating pipes coupled together. In the discussion below the pipe is generally discussed as if it is a single pipe, but this should be taken to also encompass multiple pipes coupled together, for example multiple similar sections with similar variations in cross-section and/or centre-line to produce the required turbulence.

Example implementations may include providing a stacked, coiled and/or nested arrangement of pipework with the turbulence generating elements in order to allow a significant length of pipe to be accommodated in a relatively small space. There may, for example, be a series of interconnected horizontal layers, preferably with a downward flow, i.e. towards layers below.

Turbulence at low fluid velocity in the turbulence-generating pipe, for example in a corrugated pipe, may be due to changes in cross-section area. When the fluid flows through an expansion, a negative pressure occurs at the wall. The pressure gradient forms random disruption in flow patterns similar to turbulence in a smooth pipe. The same mechanism is present even when the cross-sectional area is constant, but the pipe has bends, a cross-section which changes shape, or a helical shape, because the fluid flowing along the wall experiences expansions along the path.

Compared to a smooth straight pipe of equal diameter, turbulence can be generated at a lower fluid velocity when a turbulence-generating pipe is used. The possibility of turbulence at lower fluid velocity leads to dramatic energy savings, as flow resistance is proportional to fluid velocity to the second power. The characteristics of the turbulence-generating pipe may lead to some extra flow resistance compared to a smooth pipe of equal diameter, but not enough to offset the savings resulting from the ability to run at a reduced running speed. In addition, a lower velocity gives the additional practical advantage of a shorter tube for a given hydrolysis time.

The turbulence generating pipe may be arranged to produce turbulence more easily than pipes without the claimed repeating changes in cross-sectional area and/or centre-line. Conveniently, the turbulence generating capacity of the pipe may be defined with reference to a threshold Reynolds number, above which there will be turbulent flow. In a simplified model (fluid flowing through a straight pipe with constant round cross-section and constant fluid properties) turbulence in a pipe may be quantified by the dimensionless Reynolds number, Re, which is defined as:

$$Re = \frac{v\rho D}{\mu} \qquad \text{Equation 1}$$

Here, v is the mean velocity of the fluid, ρ is density of the fluid, D is diameter of the pipe μ is the viscosity of the fluid. The Reynolds number can be interpreted as the ratio of inertial forces to the viscous forces. It will be appreciated that as the viscosity increases or the density decreases then the flow speed must increase to maintain a set level of Reynolds number for the flow. Thus, with the same pipe geometry different flow speeds may be required to achieve turbulence with different feedstocks, or alternatively the same flow speed may be used if the geometry of the pipe is adjusted to increase the severity of the turbulence generating features.

For a straight pipe with constant round cross-section, the flow is assumed to be turbulent above a Reynolds number of 2300. For turbulence-generating pipes as described herein the transition from laminar to turbulent flow occurs at a lower Reynolds number.

Balancing the different requirements, e.g. the need for turbulent flow and sufficient drag forces to avoid sedimentation, but at the same time the slowest possible velocity in order to reduce energy consumption and tube length, gives a preferred range of Reynolds numbers. Preferably, flow of the reaction mixture within the turbulence-generating pipe is turbulent at Reynolds numbers of less than 1000, optionally at Reynolds numbers of less than 800, and optionally at Reynolds numbers of less than 600. Thus, the turbulence generating pipe may be arranged to always produce turbulent flow when the flow has a Reynolds number above a transition value of less than 1000, optionally at Reynolds numbers of less than 800, and optionally at Reynolds numbers of less than 600. That is to say, with the preferred pipe laminar flow will only be possible below a transition value of less than 1000, optionally less than 800, and optionally less than 600.

A minimum flow velocity is necessary to avoid clogging the turbulence-generating pipe with solid, slow-moving, heavy particles in the reaction mixture. This can be understood by considering a solid particle that is too heavy to follow the fluctuations of the turbulent flow, and so slows down within the flow. To move the solid through the pipe the mean drag-forces from the fluid acting on the particle must be high enough. In example implementations the plant may be arranged to operate with a flow velocity of less than 2 m/s, optionally less than 1 m/s and optionally less than 0.5 m/s.

The average diameter of the turbulence-generating pipe and flow rate of the reaction mixture are selected to give sufficient turbulence and sufficient running speed, but avoiding formation of emulsions.

It will be appreciated that the specific diameter, flow-rate and process time will need to be adjusted depending on a number of factors, including the composition of the feedstock and the particular reaction mixture to be processed, as well as the desired end product.

The process time is at least 15 minutes and may be at least 20 minutes. Typically the process time (i.e. the time which the reaction mixture takes to traverse the enzymatic processing area) will be between 90 minutes and 30 minutes, more preferably between 80 minutes and 40 minutes, and most preferably, about 50 minutes. The process time may of course vary depending on the particular reaction concerned, including factors such as the composition of the feedstock, enzyme efficiency and concentration, temperature, pH, ion conditions and the flow rates used.

The length of the turbulence generating pipe can be calculated from the desired flow rate and process time. While the overall processing time required would determine the total tube length, it might in some cases be desirable to divide the tube, i.e. the processing area, into a series of two or more successive compartments with or without an intervening pumping mechanism, in order to adjust reaction conditions such as temperature, pH and ionic conditions or substrate velocity or simply to accommodate the flow length of pipe in a given installation space.

The length of the turbulence generating pipe (series of connected pipes) may be at least 50 m, optionally at least 100 m. As will be evident from the examples discussed below the length may be considerably longer than this. The nature of the proposed arrangement is such that it allows for flexibility in adding processing stages with additional pipework and so on and it is capable of accommodating very long reaction times in a single continuous process.

The cross-section is the section transverse to the primary flow direction. A "changing cross-section" refers to a cross-section that has a changing area, a changing shape, or both a changing shape and changing area along the primary flow direction, i.e. along the extent (length) of the pipe.

In the context of the present invention, "repeatedly changing" means that the turbulence-generating pipe has a first configuration (cross-section and/or centre-line) at one location along the pipe, and a second configuration (cross-section and/or centre-line) at a second location along the pipe, and the turbulence-generating pipe repeatedly switches from one configuration to the second, and back again, along the length of the pipe. Thus the turbulence-generating pipe may conceptually be considered as comprising a number of joined-up repeating units.

The number of repeating units is typically greater than 10, more preferably greater than 20, most preferably greater than 50. The use of a turbulence generating pipe with these numbers of repeating units in a repeatedly changing cross-section and/or centre-line to generate turbulence for an enzymatic processing area is considered novel and inventive in its own right and thus, in another aspect, the invention provides a continuous flow-based enzymatic processing plant for enzymatic processing of organic molecules comprising: an enzymatic processing area, wherein the enzymatic processing area comprises a turbulence-generating pipe with a repeatedly changing centre-line and/or a repeatedly changing cross-section, for generating turbulence to mix a reaction mixture and prevent sedimentation of particles as the mixture is flowing through the turbulence-generating pipe, and wherein the enzymatic processing area comprises a turbulence generating pipe or multiple turbulence generating pipes joined together with the number of repeating units of the repeatedly changing cross-section and/or centre-line being greater than 10, more preferably greater than 20, most preferably greater than 50. The features described above and below can be used in combination with this aspect as well as with the other aspects described herein.

The frequency of repeated units may be in the range of 5 to 200 per meter, more preferably, 10 to 100 per meter. More preferably, the frequency of repeated units may be in the range of 25 to 75 per meter, and most preferably is in the range of 40 to 60 per meter.

The characteristics of the repeating units may be defined in terms of their depth (e) and width (p). The width, p, (or spacing, or pitch) of the repeating units is the distance between one point on the repeating unit and the corresponding point on the next repeating unit (analogous to the wavelength of a wave). The depth, e, is the perpendicular distance between the tangent to the extreme outermost point of the repeating unit and the tangent to the extreme innermost point of the repeating unit.

The ratio of p/e for the turbulence-generating pipe is preferably greater than 0.5, more preferably greater than 1, and most preferably greater than 2. The ratio of p/e for the turbulence-generating pipe is preferably less than 50, more preferably less than 25, and most preferably less than 10. The ratio of p/e for the turbulence-generating pipe is preferably in the range of 3 to 6.

As noted above, the cross-sectional area may change repeatedly. For example, the cross-section may decrease, then increase, then decrease again (i.e. the pipe may constrict, broaden and constrict), and so on, along the length of the pipe. The cross-section may maintain the same shape cross-section whilst periodically changing cross-sectional area, i.e. the pipe may be a corrugated pipe.

Where the turbulence-generating pipe has a changing cross-sectional area, the difference between the maximum cross-sectional area and minimum cross-sectional area may be between 20% and 3% of the average cross-sectional area, more preferably between 15% and 5% of the average cross-sectional area, and most preferably about 10% of the average cross-sectional area.

Alternatively, or in addition, the shape of the cross-section may change repeatedly. For example, the cross-section may change from a circle to an ellipse to a circle, and so on, along the length of the pipe. Other shapes may also be used for the cross section, such as polygonal shapes, Reuleaux polygons, ovals such as Cassini ovals, star shapes and so on. Preferably the cross-section does not have any sharp corners, especially internal corners. The cross-section may maintain the same cross-sectional area whilst periodically changing shape. Alternatively, the cross-sectional area may also vary.

The centre-line is the continuous line passing through the geometrical centre of the cross-sections along the length of the pipe. An unchanging centre-line, in the context of the present application, is one in which the centres of the cross-sections at either end of the pipe are joined by a straight line. A changing centre-line is one in which the centre-line does not follow such a straight line. Thus, the pipe may have multiple repeated bends. The pipe may have a helical shape, such that the centre-line is a helix.

Some or all of the bends may be 90° or greater bends, for example 180° bends, in order to run the pipe backwards and forwards through an installation space. These are preferably large radius bends (preferably having a radius of curvature of greater than 2 times the diameter of the pipe, 4 times the diameter of the pipe, or 6 times the diameter of the pipe, or greater). Use of such large radius bends reduces pressure loss within the pipe, and so reduces also the risk of clogging. However, large radius bends increase the volume of installation. The skilled person will appreciate that the radius of curvature of the bends may be chosen having consideration of the installation space available. Thus, in a small space (for example, on a ship) the bends may need to have a smaller radius of curvature compared to a similar system located in a large factory, for example.

Sharper bends may also be used if pressure loss and clogging is not a major issue. In practice, this may be for fluid without large solid particles (such that there is no danger of clogging) and low fluid velocity (which leads to low pressure loss).

Typically, the average diameter of the turbulence-generating pipe will be in the range of 20 mm to 200 mm, and preferably in the range of 40 mm to 100 mm, most preferably in the range of 50 mm to 90 mm. For example, the average diameter of the turbulence-generating pipe may be about 60 mm or about 80 mm.

If the pipe has a helical shape (such that the centre-line is a helix) then the pitch of the helical centre-line should preferably be in the range of 10 to 100 mm, more preferably in the range of 13 to 40 mm, most preferably in the range of 17 to 25 mm.

Providing a helical turbulence-generating pipe, as well as resulting in the generation of turbulent flow within the reaction mixture, also allows a longer flow length of turbulence-generating pipe to be fit within a smaller space. Here, the flow length is the length traversed by the flow through the helical turbulence-generating pipe, i.e. the length of the pipe if the helix were to be unwound and the pipe straightened out.

A section of smooth and/or straight pipe may precede or follow a section of turbulence-generating pipe or could be used in connection with bends of the tube. A smooth, straight pipe presents less resistance to the flow, and so results in reduced pressure loss, compared to a turbulence-generating pipe of equal length. If a smooth pipe is provided, the length of smooth pipe should be sufficiently small that the reaction mixture does not have time to separate out whilst traversing the smooth pipe.

It is particularly advantageous if the turbulence generating pipe is a corrugated pipe, and hence preferred arrangements make use of a corrugated pipe.

A corrugated pipe is a pipe, tube, or hose, etc. with a series of parallel ridges and grooves (alternating ridges and troughs) on its surface, wherein the ridges and grooves result in a varying cross-sectional shape and/or a varying cross-sectional area along the length of the pipe. The grooves and ridges can be formed in a circumferential (annular) pattern or run along the length of the pipe in a helical pattern (spiral) around the pipe. The helical pattern may have a single start, a double start, or multiple starts. The corrugation pattern forms the repeating unit for the turbulence generating pipe.

The ridges and troughs may have (approximately) the same shape, (that is, a trough is the mirror image of a ridge, or approximately so). The shape of the corrugations may be, or may approximate, a sin wave. In alternative preferred embodiments, the shape of the corrugations (viewed in cross-section) may resemble a plurality of perimeters of sectors of ovoid shapes (for example, ovals, circles, or ellipses) joined together.

The grooves and ridges should preferably have no sharp corners in the interior of the turbulence-generating pipe, for example the corners preferably have a radius of at least 3 mm or more, more preferably 6 mm or more. The grooves and ridges should preferably be formed without any sharp intersections between adjacent surfaces or planes in the interior of the turbulence-generating pipe, preferably with no intersections sharper than 90 degrees.

The corrugated pipe may straight, may be formed in a helical shape (as discussed above in relation to the first or second aspect), or may have multiple repeated bends (as discussed above in relation to the first or second aspect).

If the corrugated pipe has multiple bends or is formed in a helical shape, the bends or helical shape may be provided to facilitate further generation of turbulence within the corrugated pipe, or may be provided in order that a larger flow length of corrugated pipe may be provided in an installation space (as discussed above in relation to the first or second aspect). The corrugated pipe may be formed in a tight helix (similarly to the shape of a coil spring, for example). This may allow a larger flow length of corrugated pipe may be provided in an installation space. The helix may be substantially horizontal (that is, the coil axis is substantially horizontal), or substantially vertical (that is, the coil axis is substantially vertical). The helix may of course be provided in any orientation between vertical and horizontal.

The turbulence-generating pipe should be made of a suitable corrosion resistant material and may for example be made from stainless steel. In preferred embodiments the pipe may be made of a food grade acid resistant stainless steel, for example a suitable molybdenum alloyed stainless steel such as ANSI 316.

The turbulence generating pipe may include a layer of immobilised enzymes attached to the inner surface of the pipe. In such a case, the layer of immobilised enzymes is preferably provided in the system at a point downstream of a point at which solid components are separated out from the flow, such that the flow through the turbulence generating pipe may include a layer of immobilised enzymes is primarily a flow of liquid.

When the enzymatic processing is initiated, the viscosity inside the pipe may change and it may be desirable to divide the overall processing area into successive tube compartments with different diameters in order to maintain sufficient turbulent mixing and drag forces. Thus a first enzymatic processing stage of about 30 minutes to one hour (for example) may imply changes in the flow characteristics. This may be taken account of by having turbulence generating pipes of different designs and corresponding changes in flow velocity for different stages of the enzymatic processing.

From the foregoing, it will be appreciated that the proposed enzymatic processing provides a simple system with few moving parts to accommodate reaction times typical for industrial scale enzymatic processing of biological material, e.g. hydrolytic processing. The system may therefore have a lower weight compared to prior art systems arranged to process a comparable amount of reaction mixture, making it suitable for additional applications where a heavier system would not be acceptable. The system may also be easier to clean than prior art systems with active or static mixing components.

The enzymatic processing plant may include a mixing unit where water, raw material and enzymes are blended, in communication with the input of the enzymatic processing area. Correspondingly, the enzymatic processing method may include the step of pre-mixing the reaction mixture, prior to enzymatic processing.

The mixing unit may take the form of a reservoir in which the raw material, water and enzymes are combined. Provision of a mixing unit is advantageous as the reaction mixture is already crudely mixed (i.e. premixed, or partly mixed) by the time it reaches the enzymatic processing area. This reduces the period of time necessary for enzymatic processing, allowing a smaller length of turbulence-generating pipe (for a given flow velocity) compared to the case where the raw material, enzymes and water are provided in an unmixed state into the enzymatic processing area. Thus the plant is more suitable for use in an enclosed space, for example in a ship, such as a fishing vessel.

The mixing unit may be sealed (i.e. is not an open tank), and the pre-mixing may be carried out within a sealed atmosphere. This reduces the amount of oxygen to which the feedstock is exposed, and so reduced undesirable oxidation of components in the feedstock. Preferably the mixing tank does not have any significant headspace.

The enzymatic processing plant may include a first section of turbulence-generating pipe in which primary enzymatic processing (in which the enzyme catalyses a first chemical reaction) takes place and may further comprise a second section of turbulence-generating pipe configured to receive a flow of a new enzyme capable of catalysing a second chemical reaction, different from the first chemical reaction. The second chemical reaction may involve a different component of the reaction mixture from that involved in the first reaction. Furthermore, different types of enzymes may be used in different stages of the process.

For example, a first hydrolysis stage may treat protein components of the feedstock. After that stage, the oil-soluble fraction may be separated from the reaction mixture, and may subsequently be treated with lipases.

The second chemical reaction may involve the products of the primary enzymatic processing. An example is a second hydrolysis stage treating the water soluble fraction from a preceding first stage (treated with proteases) with other proteases.

Any transition from one enzymatic processing to another may be accompanied by adjustment of reaction conditions such as temperature, pH and ionic conditions. Injection points may be provided where the characteristics of the reaction mixture can be adjusted, for example for pH or ionic strength. In addition, the injection point may allow for the introduction of water. This may be necessary in case the enzyme is water soluble (and not oil soluble), but the fraction to be processed is oil-based. For the enzyme to act on the oil-based fraction, a suspension may be formed, allowing contact between the enzyme and oil-based fraction.

As an example, a first hydrolysis stage may make use of endopeptidase alcalase (Novozymes) which works best at a pH in the range of about 6.5 to 8.5 and a second hydrolysis stage may make use of acid protease A (Amano Enzyme Inc.) which works best at a pH of 2.5. Thus, the first hydrolysis stage is carried out at around neutral pH, whereas the secondary hydrolysis stage is carried out in acidic conditions.

In each section, one or more enzymes may be utilised at the same time. For example, in some embodiments proteases may be used together with other enzymes such as, for example, lipases and/or carbohydrases, during the primary enzymatic processing and optionally also or alternatively in subsequent enzymatic processing stages.

The enzymatic processing plant may include a section of turbulence-generating pipe which is configured to be heated to a temperature such that, in use, the enzymes are inactivated (deactivated, or denatured) by heat. For example, when processing fish material, it is typical to use a protease enzyme which operates optimally at 55° C. This particular protease may be inactivated by raising the temperature to about 95° C. However, it is not essential that an enzyme be deactivated prior to treatment with another enzyme.

From the foregoing discussion, it will be appreciated that it is a significant advantage for the proposed arrangement that the enzymatic processing, within what is effectively a single tube without moving parts, can be carried out at multiple temperatures. The temperature of the pipe may be controlled and adjusted by means of any suitable heat exchanger. For example the pipe may be surrounded by a heat exchange fluid, with the heat exchange fluid being flowed past the pipe and/or heated or cooled in order to provide a required temperature within the enzymatic processing area within the pipe. A tube-in-tube heat exchanger could be used. The heat exchange fluid could for example be steam or water.

The lengths of the respective sections may be chosen so as to provide the necessary processing time in each section.

The enzymatic processing plant may include a separator system. The separator system may be operable to separate water-soluble components from lipids, for example. The separator system may comprise a three-phase decanter operable to output a flow of oil (lipids, and oil-soluble components), a flow of water-soluble components, and a flow of sediment. The separator system may comprise one or more centrifuges to further separate components in the oil-soluble flow and/or components in the water-soluble flow. The separator system may also comprise one or more filters (molecular sieves or mechanical filters, for example).

The feedstock may comprise oil-based components, such as fish oils, fish liver oils, mammalian oils (for example, seal), crustacean oils (for example, krill) and molluscan oils (for example, squid), as well as oils present in marine and freshwater algae, yeast or oilseeds.

The enzymatic processing plant may be provided with a further section of turbulence-generating pipe configured to receive the output from the primary processing, for example the lipid flow and the addition of lipases to modify the lipids.

The enzymatic processing plant may be provided with a polisher for cleaning an oil-based component.

The enzymatic processing plant may be provided with a separator system and drier for separating and drying solid components of the reaction mixture. The solid components may for example be insoluble proteins, bone, shells of crustaceans (comprising carbohydrates and/or chitin).

Some form of separator system (for example, a filter) may be used to separate the insoluble proteins from the remaining solid components. The insoluble proteins and remaining solid components may then subsequently be treated separately (for example, in further enzymatic processing stages).

Any emulsified components present in the system may be separated from the main flow using a filter, and may also be included in the solid fraction to be dried in the drier.

When the feedstock contains fish material, for example, at least some of the solid components (which may also include emulsified components) may be dried to form bonemeal, or fishmeal, for example, which may be used in products such as animal feed or fertilizer.

The enzymatic processing plant may be provided with a further section of turbulence-generating pipe configured to receive at least some of the solid components and an enzyme for treating the solid components in an enzymatic processing step. For example, when processing crustaceans such as krill, the solid components will comprise chitin (from the shells of the crustaceans). This chitin may be treated with chintinases in an enzymatic hydrolysis step.

Thus the above-described components of the enzymatic processing plant may be provided as a modular system, i.e. a system having multiple stages, or multiple steps. Such a system may be configured to output a number of different products. In such a modular system, provision of a turbulence-generating pipe is not seen as essential, although it is advantageous; these concepts are considered to be independently patentable. The turbulence generating pipe more broadly the enzymatic processing area described above may advantageously be included as the enzymatic processing area described in the aspects below.

Thus, a further aspect of the present invention provides a method of manufacturing a modular enzymatic processing plant for enzymatic processing of a reaction mixture, the method comprising determining a required enzymatic processing process and manufacturing a suitable enzymatic processing plant from a kit of modular parts by providing:
  a pump for pumping the reaction mixture through the enzymatic processing plant;
  a first enzymatic processing area for performing a first stage of enzymatic processing;
  a separator system comprising a decanter for separating a flow of water soluble components, oil-soluble components and solid components;
the method further comprising:
  considering whether or not each of the following components are necessary for a processing plant capable of performing the required enzymatic processing process: a filter; a second enzymatic processing stage; a third enzymatic processing stage; a post-separator system stage; a flow division stage; and a flow combining stage;
  and, including the necessary components in the modular plant.

The method may include providing a second enzymatic processing stage. The second enzymatic processing stage may be provided downstream of the first enzymatic processing stage, and may be configured to be in communication with the first enzymatic processing area such that in use, the second enzymatic processing stage receives at least a portion of the reaction output from the first enzymatic processing area.

The method may include providing a third enzymatic processing stage. The third enzymatic processing stage may be provided downstream of the second enzymatic processing stage, and may be configured to be in communication with the second enzymatic processing area such that in use, the third enzymatic processing stage receives at least a portion of the reaction output from the second enzymatic processing area.

The method may further comprise considering whether or not each of the following post-separator system stages are necessary for a processing plant capable of providing the necessary processing: a further enzymatic processing stage, a drier or a polisher. The method may include providing a post-separator system stage.

The second and/or third processing stage(s), or further processing stage(s) may be provided downstream of the separator system, and may be configured to be in communication with the separator system such that in use, the second and/or third enzymatic processing stage receives one of the following output from the separator system: the flow of water soluble components, the flow of oil-soluble components, or the solid components.

The method may include providing a drier for drying solid components. The method may include providing a polisher for cleaning oil-soluble components.

The method may include providing a flow division stage at which the flow is divided into two or more flows. The plant may be configured such that, in use, the two or more flows are processed in different stages downstream, or one or more of the flows may be returned to an earlier stage.

The flow division stage may be provided after the first enzymatic processing stage, after the second enzymatic processing stage, after the third enzymatic processing stage, or after the separator system.

The method may include providing a flow combining stage at which, in use, a flow from downstream is combined with a flow earlier in the plant.

The flow combining stage may be provided before the first enzymatic processing stage, before the second enzymatic processing stage, before the third enzymatic processing stage, before the separator system, or before the drier.

The method may include providing an injection point prior to a stage for introducing chemicals to modify reaction conditions within the stage. The injection point may be provided before the first enzymatic processing stage, before the second enzymatic processing stage, before the third enzymatic processing stage, before the separator system, or before the drier.

The method may include providing a heat exchanger for heating or cooling a stage.

The method may include providing an enclosed mixing chamber upstream of the first enzymatic processing stage. The mixing chamber may be heated by a heat exchanger in order to bring the reaction mixture to a temperature suitable for optimal enzymatic action in the first hydrolysis stage. Alternatively or additionally, the reaction mixture may be brought up to (or close to) the required temperature by adding hot water to the feedstock. In embodiments where the enzyme is added directly into the reaction mixture in the mixing chamber, care must be taken that the enzyme is not deactivated (denatured) by the hot water, by keeping the temperature of the reaction mixture below the deactivation temperature. To avoid such a problem, the enzyme may not be added into the mixing chamber, but may instead be added to the reaction mixture through an injection point at the start of the first enzymatic processing stage.

The method may include providing a filter for separating from the reaction mixture components with a given molecular size, or larger.

The invention also extends to a kit of parts for making an enzymatic processing plant for enzymatic processing of organic compounds in a reaction mixture, the kit of parts comprising: a pump for pumping the reaction mixture through the enzymatic processing plant; a first enzymatic processing area for performing a first stage of enzymatic processing; and a separator system comprising a decanter for separating a flow of water soluble components, oil-soluble components and solid components; and the kit of parts further comprising one or more of: a filter; a second enzymatic processing stage; a third enzymatic processing stage; a flow division stage; a flow combining stage; an injection point; a mixing chamber; a polisher; and a drier.

In preferred embodiments the kit of parts comprises parts selected in order to meet the requirements of the above method of manufacturing a modular enzymatic processing plant. As noted above, the kit of parts may include an enzymatic processing area as described in relation to the earlier aspects of the invention.

A particular advantage of all the aspects and preferred arrangements above is that the system may be operated as a closed system, meaning that oxygen within the system may be minimised or at least reduced compared to prior art systems. Advantageously, oxidation of any oil components may thereby be reduced. It is preferred for the closed system to have no open tanks and no open liquid surface (i.e. any tank such as the mixing tank preferably does not have any significant headspace).

The apparatus or method of any of the embodiments above may be used on board a ship. Thus, the invention extends to cover a ship fitted with the proposed enzymatic processing plant, and to a method including carrying out enzymatic processing as described above on board a ship. The turbulence-generating tube and the use of the mixing chamber can contribute to a reduction in size and weight of the apparatus required, which is a significant advantage for shipboard use. In addition, the apparatus or method for shipboard use preferably includes operating the system without any open tank or other open liquid surface. This provides further advantages since in general any open liquid surface should be avoided onboard a ship, due to the risk of sloshing and consequent instability of the ship.

BRIEF DESCRIPTION OF THE DRAWINGS

Certain preferred embodiments will now be described in greater detail by way of example only with reference to the drawings, in which.

DETAILED DESCRIPTION OF THE INVENTION

Figure 1A:
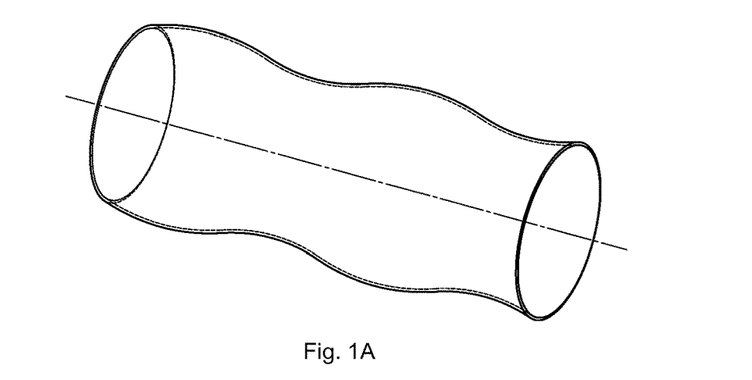
FIG. 1A shows a part of a corrugated turbulence-generating pipe.

FIG. 1A shows a part of a corrugated turbulence-generating pipe. The pipe has a diameter of about 60 mm, corrugation depth e of about 6 mm, and p/e of about 13. In such a pipe, turbulence occurs at Reynolds number above approximately 800.

Figure 1B:
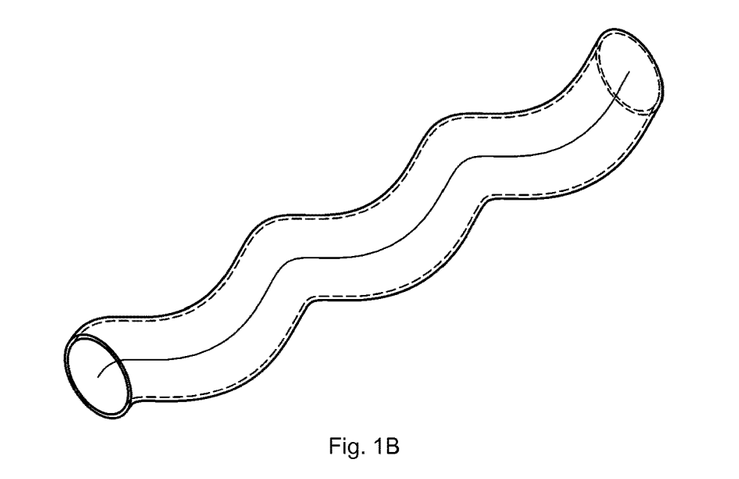
FIG. 1B shows a part of a helical turbulence-generating pipe.

FIG. 1B shows a part of a helical turbulence-generating pipe. The pipe has a diameter of about 60 mm. The pitch of the helical centre-line is 20 mm, and the radius of curvature of the helical center-line is 1.5 mm.

Figure 1C:
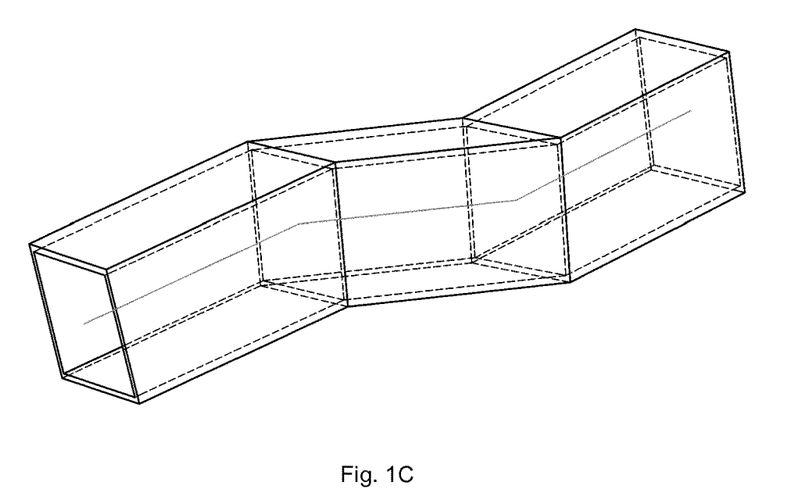
FIG. 1C shows a part of a turbulence-generating pipe having bends.

FIG. 1C shows a part of a turbulence-generating pipe having bends. The pipe has a cross-section that is square with sides of about 60 mm. The bends are at an angle in the range of 15° to 30°

Figure 1D:
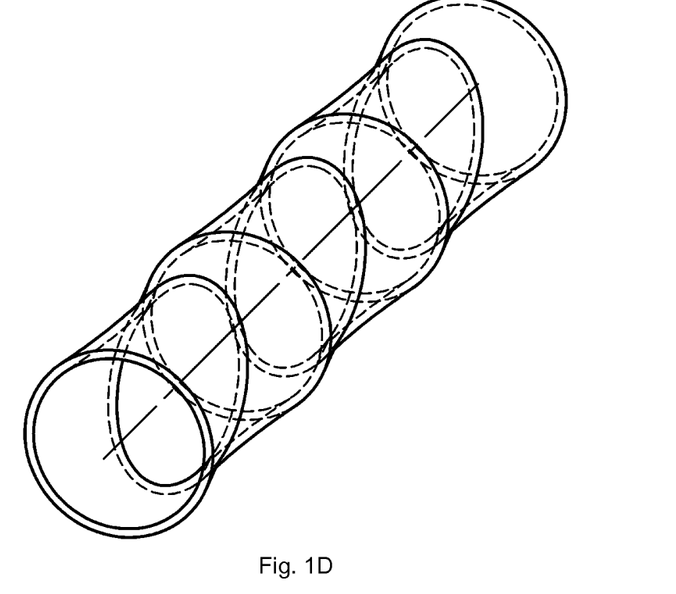
FIG. 1D shows a part of a turbulence-generating pipe having a changing cross-sectional shape.

FIG. 1D shows a part of a turbulence-generating pipe having a changing cross-sectional shape. The pipe changes from a circular cross-section to an elliptical cross-section. The cross-sectional area is about 2800 mm$^2$.

Figure 1E:
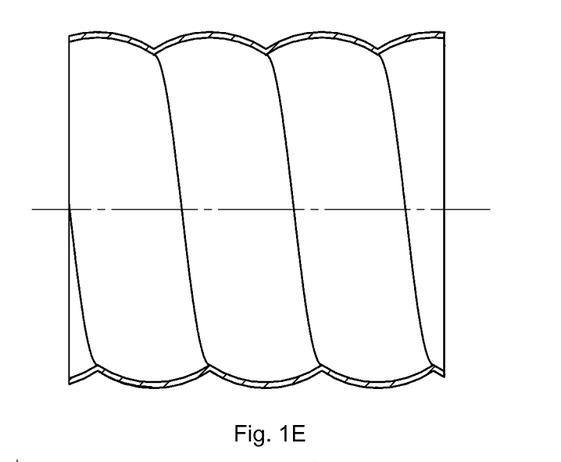
FIG. 1E is a cross-sectional view of a pipe with a helical corrugation pattern.

FIG. 1E is a cross-sectional view of a pipe with a helical corrugation pattern, the helix having a single start.

Figure 2:
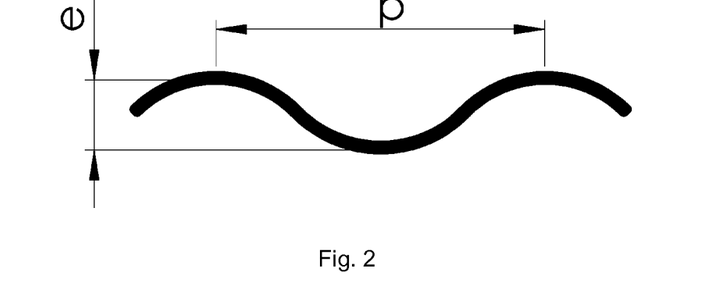
FIG. 2 shows the parameters of depth and width for a corrugated pipe.

FIG. 2 shows the pitch (width) p and depth e of corrugations on a corrugated pipe.

Figure 3:
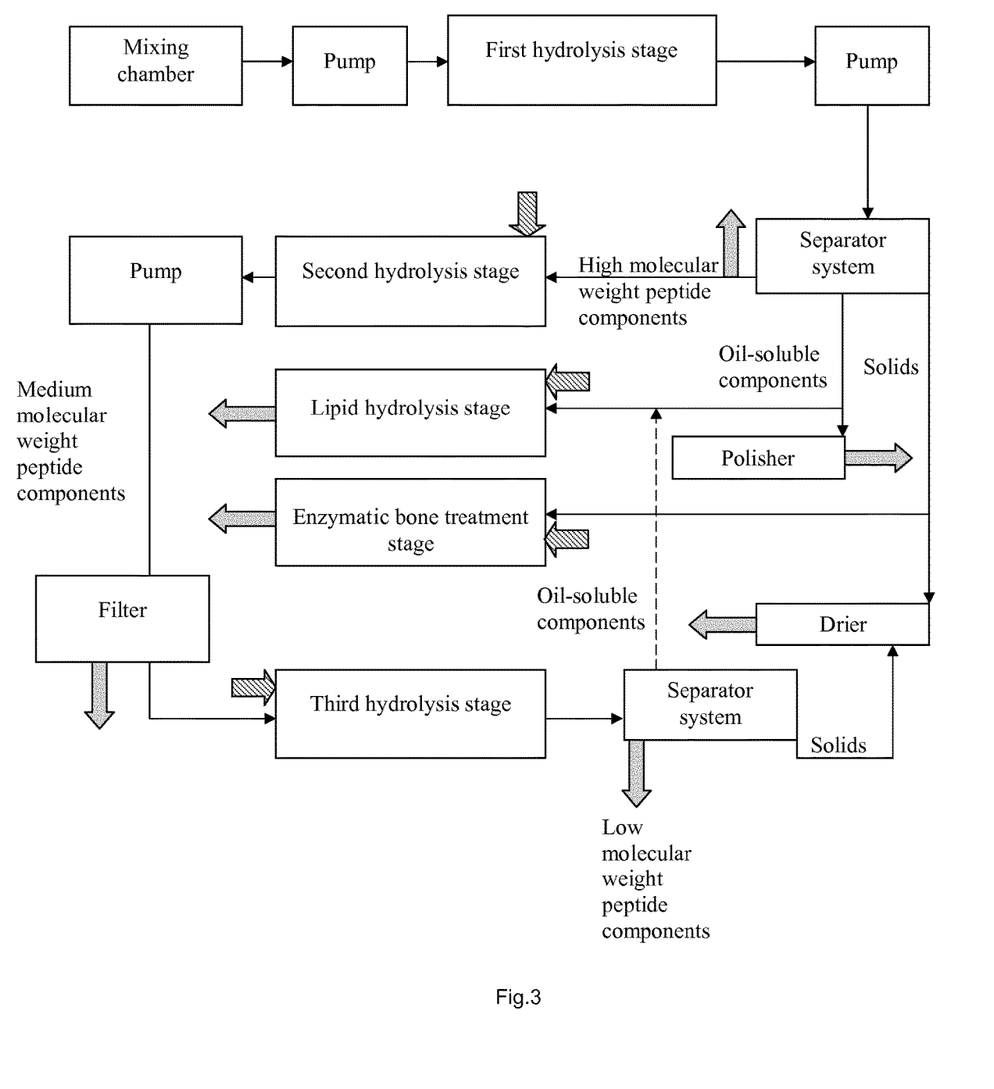
FIG. 3 shows a modular plant for enzymatic processing.

FIG. 3 shows a modular plant for enzymatic processing of organic molecules. In this case, the plant is for hydrolysis of protein in a protein-lipid mixture. The use of the plant for hydrolysis is exemplary and not limiting on the invention; it will be apparent that a similar apparatus could be used for any multi-stage enzymatic process. Further, in this case, the raw material processed by the system is fish. However, the use of the plant for processing fish is exemplary and not limiting on the invention; it will be apparent that a similar apparatus could be used with a different raw material. Further examples of processes making use of the proposed device are set out below.

The particular enzyme (and hence reaction conditions) used in each stage will depend on the raw material and the products to be obtained, and can be chosen accordingly.

The plant comprises a mixing chamber for pre-mixing the reaction mixture prior to injection into the first hydrolysis stage. Aside from an input for receiving the raw materials and an output for connection to the next section of the hydrolysis plant, the mixing chamber is sealed and has a negligible headspace, so as to reduce the amount of oxygen which is brought into contact with the reaction mixture. This reduces oxidation of oils present in the feedstock. The mixing chamber is heated by a heat exchanger in order to bring the reaction mixture to a temperature suitable for optimal enzymatic action in the first hydrolysis stage.

The fish, water, and a protease are mixed and heated in the mixing chamber. After mixing, the reaction mixture is pumped by a pump into the first hydrolysis stage. Here, protein in the reaction mixture is hydrolysed to form high-molecular weight peptides. The first hydrolysis stage is a corrugated pipe having a mean diameter of 46 mm, with a plurality of 180° bends, with radius of curvature of 200 mm.

In the first hydrolysis stage, the reaction mixture has the following properties:
Density $\rho = 1000$ kg/m$^3$
Viscosity $\mu = 0.02$ Ns Reynolds number Re=800
Mean velocity v=0.35 m/s
The volume flow rate for a given diameter is given by:

$$\dot{V} = \frac{\pi}{4} * D^2 * v \qquad \text{Equation 3}$$

For the parameter values given above, this gives a volume flow rate of 2.1 m³/h. The total length of the first hydrolysis stage is of the order of 1 km, and the processing time is of the order of 1 hour.

Towards the end of the first hydrolysis stage, the corrugated pipe is heated to a temperature hot enough to deactivate (denature) the protease.

The flow from the first hydrolysis stage is pumped using a pump to a separator system. The separator system comprises a three-phase decanter operable to output a flow of oil (lipids, and oil-soluble components), a flow of water-soluble components, and solid components.

The solid components from the separator system (primarily bone) are treated in two separate ways. A portion of the solids is passed to a drier (for example by a conveyor, not shown) and is dried to form fishmeal. The fishmeal is output as a product of the system (useful outputs of the system are shown as shaded arrows). A second portion of the solids is passed (for example by a conveyor, not shown) to a further enzymatic treatment stage for further treatment.

The further enzymatic treatment stage includes an input means for modifying the pH or ionic properties of the reaction mixture to suit the optimal operating conditions of the enzyme (shown as a hatched arrow). The product of the further enzymatic processing is output as a product of the system, after drying in a further drier (not shown).

The oil-soluble components from the separator system are also treated in two separate ways. A portion of the oil-soluble components is passed to a polisher (using a pump, not shown) which cleans the oil. The cleaned oil is separated into component parts using a centrifuge and filter (not shown) and the resultant components are output as products of the system. A second portion of the oil-soluble components is passed to a lipid hydrolysis stage (using a pump, not shown) and is treated with lipases. The lipid hydrolysis stage includes an input means (shown as a hatched arrow) for modifying the pH or ionic properties of the reaction mixture to suit the optimal operating conditions of the lipase. In addition, the input means allows for the introduction of water. This is necessary since lipases are water soluble (not oil-soluble). Thus, for the lipase to act on the lipids, a suspension may be formed, allowing contact between the lipase and lipids. Provision of a turbulence generation pipe which mixes efficiently but minimizes the formation of emulsions is useful in such a process. The product of the lipase processing is output as a product of the system.

The water-soluble components from the separator system are also treated in two separate ways. A portion of the high-molecular weight peptide components are filtered out (using a filter, not shown) and are output from the system as a product. The remaining portion is input into a second hydrolysis stage.

The second hydrolysis stage includes an input means (shown as a hatched arrow) for modifying the pH or ionic properties of the reaction mixture to suit the optimal operating conditions of the second protease. The protease hydrolyses high-molecular weight peptide components to form medium-molecular weight peptide components. Towards the end of the second hydrolysis stage, the second hydrolysis stage is heated to a temperature hot enough to deactivate the protease.

From the second hydrolysis stage, a portion of the medium-molecular weight peptide components are filtered out using a filter and are output from the system as a product. The remaining portion is input into a third hydrolysis stage.

The third hydrolysis stage includes an input means for modifying the pH or ionic properties of the reaction mixture to suit the optimal operating conditions of the third protease (shown as a hatched arrow). The protease hydrolyses medium molecular weight peptide components to form low-molecular weight peptide components.

Towards the end of the third hydrolysis stage, the third hydrolysis stage may, if needed, be heated to a temperature hot enough to deactivate (denature) the protease.

From the third hydrolysis stage, the reaction mixture is passed to a separator system, which separates low-molecular weight peptide components from any remaining solids or oil soluble components. Any solid components are passed back to the drier (or the enzymatic bone treatment stage) and any oil components are passed back to the lipid hydrolysis stage (or the polisher). The low-molecular weight peptide components are output from the system.

The skilled person will appreciate that not all of these components are essential, and depending on the raw materials and desired end products, a combination of the elements of this system will be employed.

The processing plant may be used for other processes as well, and it provides advantages for any process requiring relatively long reaction times. Various possible processes are set out in the examples below:

Example Hydrolysis Process 1

The process uses whole sardines (anchovy) with Alcalase (Novozymes), ground through 6 mm dyes, a raw material/water ratio 50/50 (w/w), and a reaction temperature 60° C. Targeted % DH=17 (% DH=number of peptide bonds cleaved/total number of peptide bonds), estimated reaction time 45 minutes based on info from the enzyme manufacturer. The enzyme added is 0.1% (d.w) of raw material (w.w) excluding added water. The plant is operated with a capacity 7 MT per hour, of which 3.5 MT of fish and 3.5 MT of water. The tube length will be 863 m.
Supplementary information: In this case no large bone particles are present, and thus the risk of clogging due to sedimentation of hard particles is low. The whole length of the tube is of similar shape and diameter throughout, although viscosity decreases down the line. A boost pump is fitted in ⅓ the length from the inlet as a safety guard towards clogging. The concentration of peptides increases with time as protein hydrolysis goes on. Peptides can act as emulgators, and a key point is to avoid the formation of emulsions along the tube.
Reaction Mixture Properties:
  Density $\rho$=1000 kg/m³
  Viscosity $\mu$=25 cP (inlet
Selected Properties of the Flow:
  Reynolds number Re=1125
  Mean velocity v=0.32 m/s
Using these parameters gives the diameter D=88 mm.
For the parameter values given above, this example has a volume flow rate of 7 m³/h.

Example Hydrolysis Process 2

This example uses heads and backbones from salmon to be hydrolysed using Protamex (Novozymes). The enzyme concentration is 0.1% (d.w) of raw material (w.w). The raw material undergoes grinding through 6 mm dyes, and is mixed in a ratio of raw material/water 50/50 (w/w), before being processed at a reaction temperature of 50° C. The targeted degree of hydrolysis % DH=10 (% DH=number of peptide bonds cleaved/total number of peptide bonds), and the estimated reaction time 30 minutes based on information from the enzyme manufacturer.

Supplementary information: In this case where large bone particles are present the optimal configuration of the hydrolysis unit is a first part (⅓) where there is less risk of sedimentation of the bone particles resulting in a clogged tube—due to relative high viscosity. As process runs then the viscosity declines increasing the risk of clogging. Therefore, in this embodiment the hydrolysis unit is constructed by means of three different tube diameters linked together.

The hydrolysis unit parameters are given below for the pipe inlet, at the mid-length and at the pipe outlet.

Reaction Mixture Properties:
   Density $\rho$=1000 kg/m$^3$
   Viscosity $\mu$=23 cP, 17 cP and 9 cP
Selected Properties of the Flow:
   Reynolds number Re=1035, 1655, 3620
   Mean velocity v=0.23 m/s, 0.32 m/s and 0.43 m/s
Using these parameters gives diameters of D=104 mm start, 88 mm in mid-section and 76 mm the last part. The total tube length is 586, distributed into 137 m first part, 192 m mid part and 257 m last part. There will be a boost pump before section 2 and before section 3.

The volume flow rate for this example would be 7 m$^3$/h.

Example Hydrolysis Process 3

In this case hydrolysate processed from salmon frames and heads by means of Alcalase (Novozymes) is further processed through a secondary hydrolysis using Flavourzyme (Novozymes) which is an exopeptidase/endopeptidase complex specially designed to optimize taste and reduce bitterness. The hydrolysate was diluted to contain 10% dry matter, of which protein is the major part (approx. 90%). The substrate contains virtually no lipids. The reaction time is 20 minutes and the reaction temperature 55° C. The enzyme concentration is 0.1% (d.w) of raw material (w.w).

Supplementary information: In this case the substrate is a free-flowing liquid with no particles nor lipids are present, and thus there is no risk of clogging or formation of emulsions. Viscosity is low throughout the process tube, which is of similar construction throughout.

The following exemplary calculation uses values for the parameters which may be typical of a working system:

Reaction Mixture Properties:
   Density $\rho$=1040 kg/m$^3$
   Viscosity $\mu$=6.5 cP
Selected Properties of the Flow:
   Reynolds number Re=1811
   Mean velocity v=0.09 m/s
Using these parameters gives the pipe diameter D=125 mm. The tube length is 109 m.

For the parameter values given above, the volume flow rate is 4 m$^3$/h.

It should be apparent that the foregoing relates only to the preferred embodiments of the present application and the resultant patent. Numerous changes and modification may be made herein by one of ordinary skill in the art without departing from the general spirit and scope of the invention as defined by the following claims and, the equivalents thereof.

We claim:

1. An enzymatic processing plant for continuous flow-based enzymatic processing of organic molecules, comprising:
   an enzymatic processing area, wherein the enzymatic processing area comprises a turbulence-generating pipe with a repeatedly changing centre-line and/or a repeatedly changing cross-section, for generating turbulence to mix a reaction mixture and prevent sedimentation of particles as the reaction mixture is flowing through the turbulence-generating pipe,
   wherein the turbulence-generating pipe is provided in a stacked, coiled or nested arrangement, in one or more broadly horizontal layers,
   wherein the enzymatic processing plant and the enzymatic processing area are arranged such that the reaction mixture is subjected to turbulence within the enzymatic processing area for a reaction time of 15 minutes or more,
   wherein turbulence is generated in the turbulence generating pipe without moving parts, and is generated throughout the bulk of the flow,
   wherein the turbulence-generating pipe comprises a number of notional repeating units, wherein the number of repeating units is greater than 10,
   wherein the plant is arranged to operate with the reaction mixture having a flow velocity of less than 2 m/s through the turbulence generating pipe,
   wherein the enzymatic processing area includes one or more turbulence generating pipe(s) with a total length of at least 50 m, and
   wherein the turbulence-generating pipe has an average diameter in the range of 20 mm to 200 mm.

2. A plant as claimed in claim 1, wherein the reaction time is more than 30 minutes.

3. A plant as claimed in claim 1, wherein the turbulence-generating pipe has a changing cross-sectional area.

4. A plant as claimed in claim 1, wherein the turbulence-generating pipe is a corrugated pipe.

5. A plant as claimed in claim 1, wherein the flow of the reaction mixture within the turbulence-generating pipe is turbulent at Reynolds numbers of less than 1000.

6. A plant as claimed in claim 1, wherein the turbulence generating pipe includes a layer of immobilised enzymes attached to the inner surface of the pipe.

7. A plant as claimed in claim 1, comprising an injection point for introducing reagents which change the characteristics of the reaction mixture, wherein the reagent is an acid, a base or water.

8. A plant as claimed in claim 1, comprising a heat exchanger for heating at least a portion of the turbulence-generating pipe.

9. A plant as claimed in claim 1, comprising a separator system comprising a three-phase decanter operable to output a flow of oil and oil-soluble components, a flow of water-soluble components, and a flow of sediment, and/or a centrifuges and/or a filter.

10. A plant as claimed in claim 1, wherein the plant is a modular system.

11. A ship fitted with the plant of claim 1.

12. A plant as claimed in claim 1, wherein the reaction time is less than 90 minutes.

* * * * *